United States Patent
Smith et al.

(10) Patent No.: US 7,988,624 B2
(45) Date of Patent: Aug. 2, 2011

(54) DEVICES AND METHODS FOR PERCUTANEOUS TISSUE RETRACTION AND SURGERY

(75) Inventors: Maurice M. Smith, Cordova, TN (US); Kevin T. Foley, Germantown, TN (US); Roy Lim, Cordova, TN (US); Thomas E. Roehm, III, Braden, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 989 days.

(21) Appl. No.: 11/639,517

(22) Filed: Dec. 14, 2006

(65) Prior Publication Data
US 2007/0118023 A1    May 24, 2007

Related U.S. Application Data

(63) Continuation of application No. 10/117,440, filed on Apr. 5, 2002, now Pat. No. 7,261,688.

(51) Int. Cl.
*A61B 1/32* (2006.01)

(52) U.S. Cl. .............. 600/210; 600/219; 600/225

(58) Field of Classification Search .......... 600/201–246; 606/86 R, 86 B, 915–916, 205–209
See application file for complete search history.

(56) References Cited

U.S. PATENT DOCUMENTS

| | | |
|---|---|---|
| 52,014 A | 1/1866 | Bartlett |
| 751,475 A | 2/1904 | DeVilbiss |
| 1,222,478 A | 4/1917 | Sheaff |
| 1,796,072 A | 3/1931 | Baer |
| 2,300,040 A | 10/1942 | Betts |
| 2,320,709 A | 6/1943 | Arneson |
| 2,807,259 A | 9/1957 | Guerriero |
| 3,044,461 A | 7/1962 | Murdock et al. |
| 3,747,592 A | 7/1973 | Santos |
| 3,752,149 A | 8/1973 | Ungar et al. |
| 3,788,318 A | 1/1974 | Kim et al. |
| 3,789,829 A | 2/1974 | Hasson |
| 3,807,393 A | 4/1974 | McDonald |
| 3,841,317 A | 10/1974 | Awais |
| 3,890,961 A | 6/1975 | Moore et al. |
| 3,985,125 A | 10/1976 | Rose |
| 4,263,899 A | 4/1981 | Burgin |
| 4,385,626 A | 5/1983 | Danz |
| 4,545,374 A | 10/1985 | Jacobson |
| 4,716,901 A | 1/1988 | Jackson et al. |

(Continued)

FOREIGN PATENT DOCUMENTS

DE    200 16 971 U1    1/2001

(Continued)

OTHER PUBLICATIONS

Foley, K.T., Smith, M.M. Microendoscopic Discectomy; Techniques in Neurosurgery, vol. 3, No. 4, pp. 301-307, 1997, USA.

(Continued)

*Primary Examiner* — Eduardo C Robert
*Assistant Examiner* — Jan Christopher Merene

(57) ABSTRACT

Methods and devices for performing percutaneous surgery in a patient are provided. A retractor includes a working channel formed by a first portion coupled to a second portion. The first and second portions are movable relative to one another from an unexpanded configuration to an expanded configuration to increase the size of the working channel along the length of the working channel while minimizing trauma to skin and tissue.

11 Claims, 12 Drawing Sheets

U.S. PATENT DOCUMENTS

| | | | |
|---|---|---|---|
| 4,747,394 | A | 5/1988 | Watanabe |
| 4,765,311 | A | 8/1988 | Kulik et al. |
| 4,807,600 | A | 2/1989 | Hayes |
| 4,817,587 | A | 4/1989 | Janese |
| 4,862,891 | A | 9/1989 | Smith |
| 4,899,729 | A | 2/1990 | Gill et al. |
| 4,989,587 | A | 2/1991 | Farley |
| 5,088,472 | A | 2/1992 | Fakhrai |
| 5,139,511 | A | 8/1992 | Gill et al. |
| 5,158,545 | A | 10/1992 | Trudell et al. |
| 5,163,949 | A | 11/1992 | Bonutti |
| 5,171,279 | A | 12/1992 | Mathews |
| 5,197,971 | A | 3/1993 | Bonutti |
| 5,312,417 | A | 5/1994 | Wilk |
| 5,339,803 | A | 8/1994 | Mayzels et al. |
| 5,342,384 | A | 8/1994 | Sugarbaker |
| 5,353,784 | A | 10/1994 | Nady-Mohamed |
| 5,363,841 | A | 11/1994 | Coker |
| 5,377,667 | A | 1/1995 | Patton et al. |
| 5,389,080 | A | 2/1995 | Yoon |
| 5,490,819 | A | 2/1996 | Nicholas et al. |
| 5,503,617 | A | 4/1996 | Jako |
| 5,512,038 | A | 4/1996 | O'Neal et al. |
| 5,549,595 | A | 8/1996 | Freitas |
| 5,573,517 | A | 11/1996 | Bonutti et al. |
| 5,674,240 | A | 10/1997 | Bonutti et al. |
| 5,681,265 | A | 10/1997 | Maeda et al. |
| 5,707,359 | A | 1/1998 | Bufalini |
| 5,755,732 | A | 5/1998 | Green et al. |
| 5,785,648 | A | 7/1998 | Min |
| 5,788,630 | A | 8/1998 | Furnish |
| 5,792,044 | A | 8/1998 | Foley et al. |
| 5,795,291 | A | 8/1998 | Koros et al. |
| 5,823,947 | A | 10/1998 | Yoon et al. |
| 5,846,249 | A | 12/1998 | Thompson |
| 5,868,668 | A | 2/1999 | Weiss |
| 5,888,196 | A | 3/1999 | Bonutti |
| 5,899,854 | A | 5/1999 | Slishman |
| 5,928,139 | A | 7/1999 | Koros et al. |
| 5,931,777 | A | 8/1999 | Sava |
| 5,944,658 | A | 8/1999 | Koros et al. |
| 5,951,466 | A | 9/1999 | Segermark et al. |
| 5,954,635 | A | 9/1999 | Foley et al. |
| 5,961,499 | A | 10/1999 | Bonutti et al. |
| 5,976,146 | A | 11/1999 | Ogawa et al. |
| 5,993,385 | A | 11/1999 | Johnston et al. |
| 6,004,341 | A | 12/1999 | Zhu et al. |
| 6,024,696 | A | 2/2000 | Hoftman et al. |
| 6,027,518 | A | 2/2000 | Gaber |
| 6,042,540 | A | 3/2000 | Johnston et al. |
| 6,074,380 | A | 6/2000 | Byrne et al. |
| 6,096,046 | A | 8/2000 | Weiss |
| 6,099,547 | A | 8/2000 | Gellman et al. |
| 6,139,493 | A | 10/2000 | Koros et al. |
| 6,162,236 | A | 12/2000 | Osada |
| 6,171,299 | B1 | 1/2001 | Bonutti |
| 6,187,000 | B1 | 2/2001 | Davison et al. |
| 6,200,322 | B1 | 3/2001 | Branch et al. |
| 6,224,545 | B1 | 5/2001 | Cocchia et al. |
| 6,287,322 | B1 | 9/2001 | Zhu et al. |
| 6,302,842 | B1 | 10/2001 | Auerbach et al. |
| 6,309,349 | B1 | 10/2001 | Bertolero et al. |
| 6,312,443 | B1 | 11/2001 | Stone |
| 6,325,812 | B1 | 12/2001 | Dubrul et al. |
| 6,371,911 | B1 | 4/2002 | Hossain et al. |
| 6,416,467 | B1 | 7/2002 | McMillin et al. |
| 6,450,952 | B1 | 9/2002 | Rioux et al. |
| 6,520,907 | B1 | 2/2003 | Foley et al. |
| 6,712,795 | B1 | 3/2004 | Cohen |
| 6,749,563 | B2 | 6/2004 | Stihl |
| 6,793,656 | B1 | 9/2004 | Mathews |
| 6,851,430 | B2 | 2/2005 | Tsou |
| 6,945,933 | B2 * | 9/2005 | Branch et al. ............ 600/210 |
| 7,182,729 | B2 * | 2/2007 | Abdelgany et al. ........ 600/219 |
| 7,261,688 | B2 | 8/2007 | Smith |
| 7,473,222 | B2 | 1/2009 | Dewey et al. |
| 7,513,869 | B2 | 4/2009 | Branch et al. |
| 7,524,285 | B2 | 4/2009 | Branch et al. |
| 7,645,232 | B2 * | 1/2010 | Shluzas ................... 600/219 |
| 2001/0049498 | A1 | 12/2001 | Davison et al. |
| 2002/0107574 | A1 * | 8/2002 | Boehm et al. ............ 623/17.16 |
| 2002/0173798 | A1 | 11/2002 | DiPoto |
| 2004/0176763 | A1 | 9/2004 | Foley et al. |
| 2004/0186346 | A1 | 9/2004 | Smith et al. |
| 2005/0043742 | A1 * | 2/2005 | Bruneau et al. ............ 606/99 |
| 2005/0075644 | A1 * | 4/2005 | DiPoto et al. ............ 606/90 |
| 2007/0270655 | A1 | 11/2007 | Smith et al. |
| 2009/0156902 | A1 | 6/2009 | Dewey et al. |
| 2009/0203967 | A1 | 8/2009 | Branch et al. |

FOREIGN PATENT DOCUMENTS

| | | |
|---|---|---|
| EP | 0 455 282 A2 | 11/1991 |
| EP | 1192905 | 4/2002 |
| FR | 613342 | 11/1926 |
| FR | 2 702 364 | 9/1994 |
| FR | 2807313 | 4/2000 |
| JP | 08-13303 | 2/1996 |
| RU | 2 019 136 C1 | 9/1994 |
| RU | 2 157 656 C2 | 10/2000 |
| RU | 2 192 177 C2 | 6/2002 |
| WO | WO 83/03189 | 9/1983 |
| WO | WO 93/20741 | 10/1993 |
| WO | WO 0134019 | 5/2001 |

OTHER PUBLICATIONS

Wolfhard Caspar, Technique of Microsurgery, Microsurgery of the Lumbar Spine, Dec. 1989, pp. 105-122, Chapter 12, excerpted with permission from "The Microsurgical Technique for Herniated Lumbar Disc Operations" by Wolfhard Caspar, Aesculap Scientific Information, ed 20, Copyright 1988.

Kevin T. Foley et al., Microendoscopic Discectomy, Techniques in Neurosurgery, Dec. 1997, pp. 301-307, vol. 3 No. 4, Copyright 1997 Lippincott Raven Publishers, Philadelphia.

Luca Papavero et al., the Lumbar Microdiscectomy, Acta Orthop Scand (Suppl 251), 1993, pp. 34-37, col. 64.

John A. Mcculloch et al., Instrumentation for Spinal Microsurgery, Including Ancillary Equipment, Chapter 2, Essentials of Spinal Microsurgery, 1998, pp. 19-42, Lippincott-Raven Publishers, Philadelphia.

Dr. Wolfhard Caspar, M.D., the Microsurgical Technique for Herniated Lumbar Disk Operations and other Pathologic Processes of and around the Lumbar Disk Space, Aesculap Scientific Information, 4 page, Chapter 20, 4th Edition.

Papavero-Caspar, Transsphenoidales Hypophysenspekulum, Transsphenoidal Speculum for Pituitary Surgery, 6 pages, Aesculap.

Caspar Cervical Retractor System, 14 pages, Cat. No. C20111, Edition Jan. 2000, Aesculap Ag & Co. Kg, Tuttlingen, Germany.

Standard Surgical Instruments, Medical Department U.S. Army, 1920, 23 pages, Annex W, R26, 4567C, National Library of Medicine, Bethesda 14, Maryland.

Miltex, Gynecological and Obstetrical Instruments, 1996, 1 pg.

V. Mueller, the Surgical Armamentarium, Instruments-Professional Equipment, 1973, 2 pages, Rand McNally & Company.

DeVilbiss Vaginal Speculum, Dittrick Museum of Medical History, 1971, 8 pgs.

DeVilbiss Vaginal Speculum, Dittrick Museum of Medical History, 1981, 7 pgs.

Catalogue of Surgical Instruments and Appliances, 1904, 7 pgs., Manufactured and Sold by Philip Harris & Co., Ltd., Birmingham.

Illustrated Catalogue of Surgical and Scientific Instruments and Appliances, Hospital & Invalid Furniture Sterilizers, Nursing Requisites, First Aid Equipment, Etc., 1920, 2 pages, 7th Edition, the Surgical Manufacturing Co., Ltd., London.

William L. Reid, M.D., On the Vaginal Speculum, with a Description, a New Form of the Instrument, The American Journal of Obstetrics and Diseases of Women and Children, Mar. 1883, 7 pgs., vol. XVI No. 3.

W.L. Reid. M.D., New Bivalve Speculum, The Transactions of the Edinburgh Obstetrical Society, 1883, 5 pgs., vol. VIII, Session 1882-83, Edinburgh: Oliver and Boyd, Publishers to the Society.

John Thorburn, MD., M.R.C.P, A Practical Treatise on the Diseases of Women, Prepared with Special Reference to the Wants of the General Practitioner and Advanced Student, 1887, 5 pgs., Samuel M. Miller, M.D., Medical Publisher, Philadelphia.

James V. Ricci, M.D., The Vaginal Speculum and its Modifications Throughout the Ages, 1949, 29 pages, Reprinted from the Transactions of the Gynaecological Department of the City Hospital, 1948-1949, New York.

Illustrated Catalogue of Surgical Instruments, Medical Appliances, Diagnostic Apparatus, Etc., 8 pgs., Hynson, Westcott & Co., Baltimore, Maryland.

Surgical and Dental Instruments, 6 pgs., Noyes Bros. & Cutler, St. Paul, Minnesota.

Davenport, Diseases of Women: A Manual of Gynecology Designed Especially for the Use of Students and General Practitioners, Goodell's Speculum, 1898, p. 71-72.

Clinical Gynecology, Medical and Surgical, for Students and Practitioners, Methods of Gynecological Examinations,1894, p. 47-48, Keating & Coe ed.

Massey, Conservative Gynecology and Electro-Therapeutics, Examination of Pelvis, 1909, p. 17-18.

Winckel, Diseases of Women: A Handbook for Physicians and Students, Nutritive Disturbances of the Vagina, 1887, p. 173.

Ashton, A Text-Book on the Practice of Gynecology for Practitioners and Students, The Vagina, 1916, p. 228-232.

Goodell's Speculum, Dittrick Museum of Medical History, 1978, 14 pgs.

Teresa Riordan, A businessman invents a device to give laparoscopic surgeons a better view of their work, Mar. 29, 2004, 1 page, The New York Times.

DeVilbiss Vaginal Speculum, 2 pgs.

E.E. Montgomery, M.D., Endometritis: Uterine Dilatation and Drainage, Medical News, Feb. 2, 1892, p. 404-407.

E.J. Smith et al., Smiths' Reference and Illustrated Guide to Surgical Instruments, 1983, 75 pgs., J.B Lippincott Company, Philadelphia.

\* cited by examiner

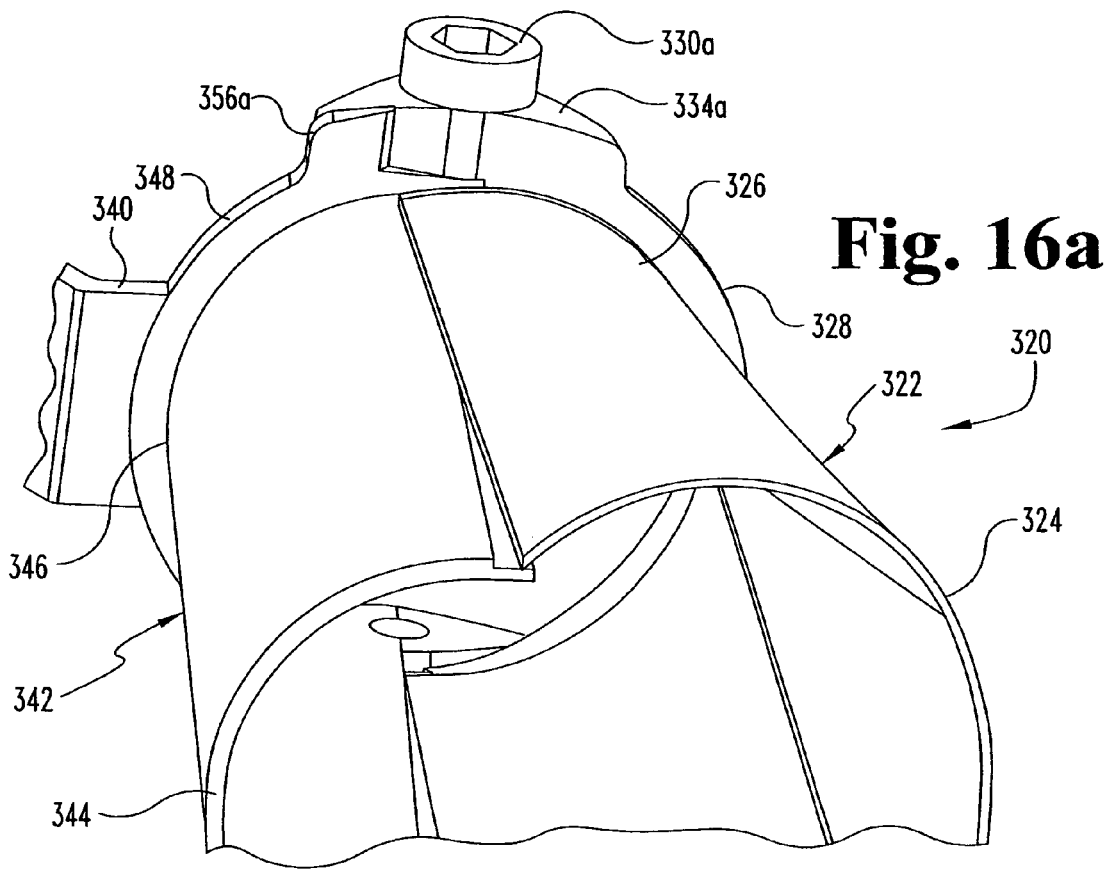
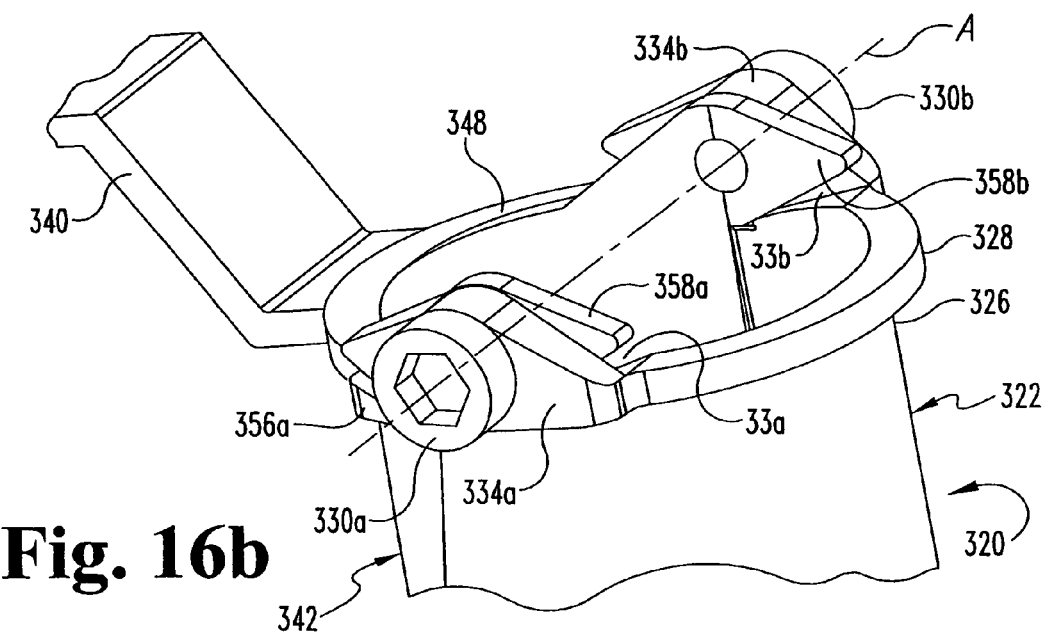

DEVICES AND METHODS FOR PERCUTANEOUS TISSUE RETRACTION AND SURGERY

CROSS-REFERENCE TO RELATED APPLICATIONS

This application is a divisional application of U.S. patent application Ser. No. 10/117,440 filed on Apr. 5, 2002, now issued as U.S. Pat. No. 7,261,688 on Aug. 28, 2007, which is incorporated herein by reference in its entirety.

BACKGROUND

The present invention relates to devices, instruments and methods for performing percutaneous surgeries.

Traditional surgical procedures for pathologies located deep within the body can cause significant trauma to the intervening tissues. These open procedures often require a long incision, extensive muscle stripping, prolonged retraction of tissues, denervation and devascularization of tissue. These surgeries can require operating room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal muscle and tissue dissection is required and the procedures can be performed under local anesthesia. For example, minimally invasive surgical techniques are desirable for spinal and neurosurgical applications because of the need for access to locations deep within the body and the danger of damage to vital intervening tissues. While developments in minimally invasive surgery are steps in the right direction, there remains a need for further development in minimally invasive surgical devices and techniques.

SUMMARY

The present invention is directed to methods and devices for performing surgery in a patient. One specific application concerns devices, instruments and techniques for percutaneous, minimally invasive spinal surgery. A further specific application includes percutaneous tissue retraction to provide access to the surgical location in the patient. Another specific application includes surgery performed through the percutaneously retracted tissue under direct vision at any location in the body. Also contemplated are surgical methods and techniques employing the instruments and devices described herein.

DESCRIPTION OF THE FIGURES

FIGS. 16a-16b illustrate another embodiment expandable retractor.

DESCRIPTION OF THE ILLUSTRATED EMBODIMENTS

Figure 1:
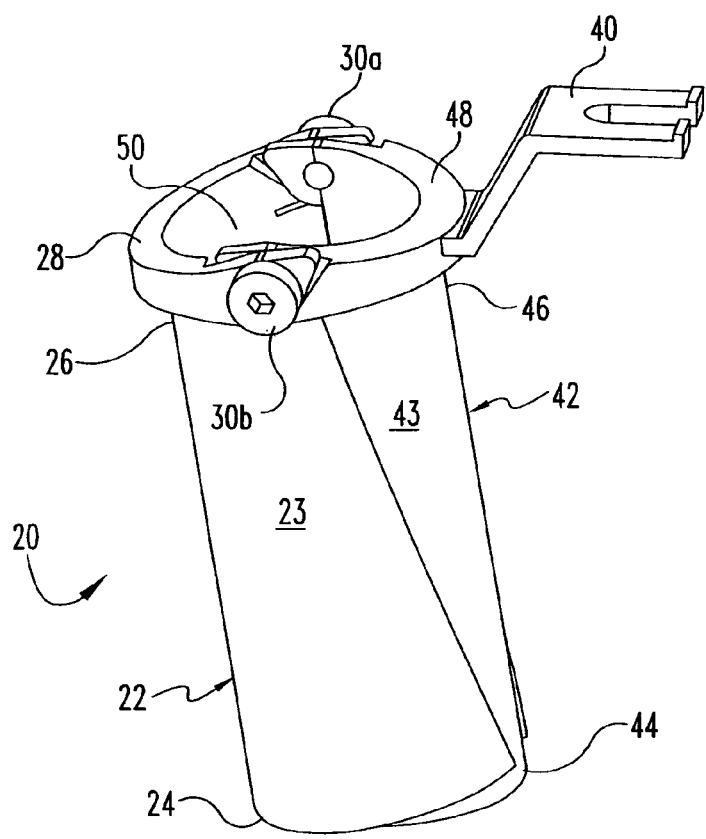
FIG. 1 is a perspective view looking toward one side of a retractor in an unexpanded configuration.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and such further applications of the principles of the invention as illustrated herein are contemplated as would normally occur to one skilled in the art to which the invention relates.

The present invention provides instruments and methods for performing percutaneous surgery, including spinal surgeries that include one or more techniques such as laminotomy, laminectomy, foramenotomy, facetectomy, discectomy, interbody fusion, spinal nucleus or disc replacement, and implant insertion, for example. The surgery is performed through a working channel or passageway provided by a retractor. Viewing of the surgical site at the working end of the retractor can be accomplished with optics mounted on the retractor, positioned over the retractor, and/or through a viewing system such as lateral fluoroscopy. The retractor is expandable in situ to increase the size of the working channel to facilitate access to the working space at the distal end of the retractor while minimizing trauma to tissue surrounding the retractor. The retractor can be used with any surgical approach to the spine, including anterior, posterior, posterior mid-line, lateral, postero-lateral, and/or antero-lateral approaches, and in other regions besides the spine.

Figure 2:
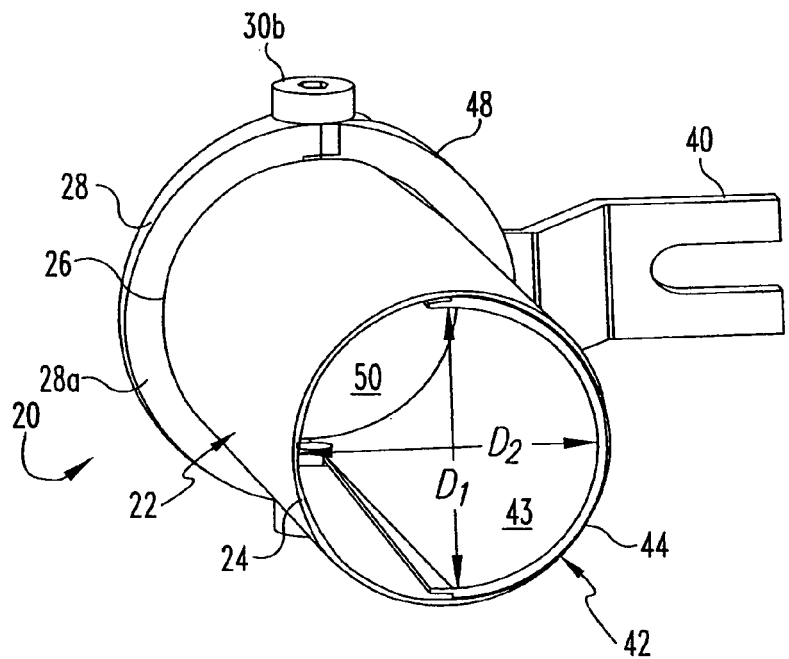
FIG. 2 is a perspective view looking toward the bottom of the retractor of FIG. 1.
Figure 3:
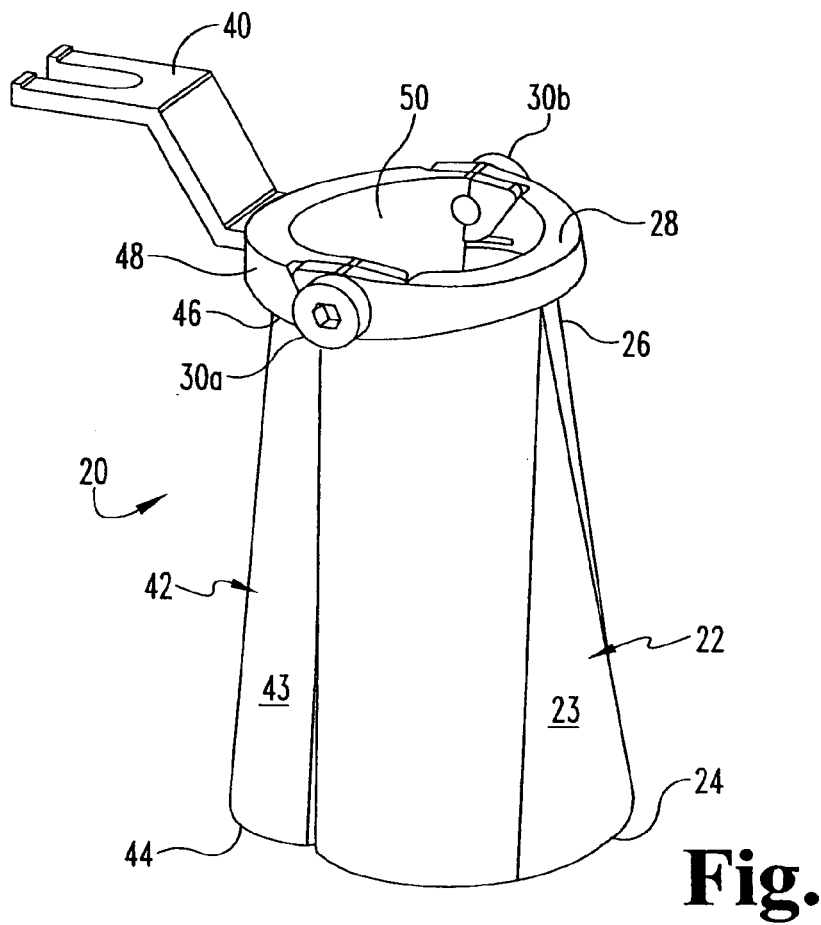
FIG. 3 is a perspective view looking toward the other side of the retractor of FIG. 1 with the retractor in an expanded configuration.
Figure 4:
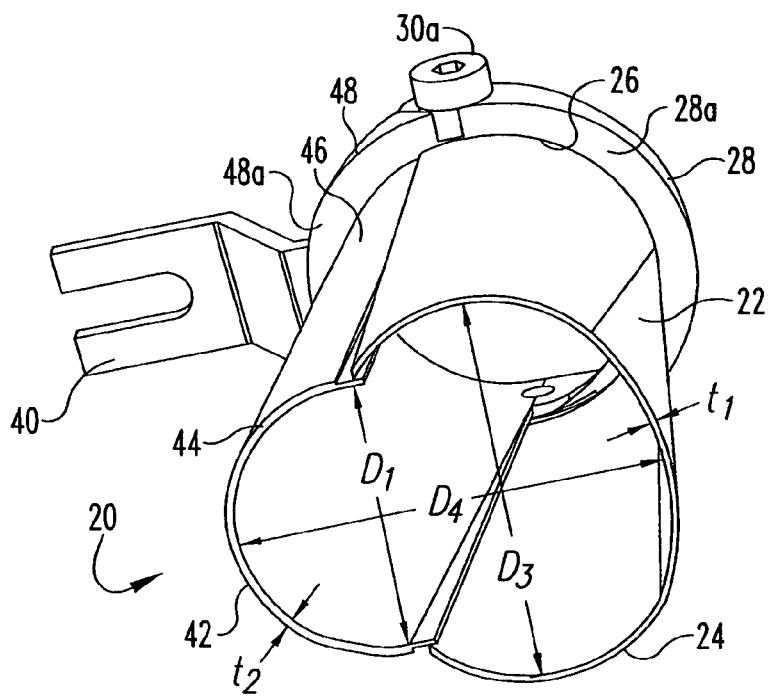
FIG. 4 is a perspective view looking toward the bottom of the expanded retractor of FIG. 3.

In FIGS. 1-2 there is illustrated a retractor 20 that includes a first portion 22 coupled to a second portion 42. First portion 22 has a distal end 24 and an opposite proximal end 26. Second portion 42 has a distal end 44 and an opposite proximal end 46. In the illustrated embodiment, first portion 22 is pivotally coupled to second portion 42 at proximal ends 26, 46. A working channel 50 is formed by first portion 22 and second portion 42. Working channel 50 extends between and opens at distal ends 24, 44 and proximal ends 26, 46. Retractor 20 is movable to an expanded configuration, as shown in FIGS. 3-4, by pivoting first portion 22 and second portion 42 relative to one another about proximal ends 26, 46. Other coupling arrangements are also contemplated that allow first portion and second portion 42 to be moved away from one another to expand retractor 20 and increase the size of working channel 50 between its distal and proximal ends.

Retractor 20 is insertable through skin and tissue of a patient to provide working channel 50 to the surgical site. It is contemplated that retractor 20 is inserted through the skin and tissue in an unexpanded configuration, such as shown in FIGS. 1-2. After insertion into the patient, retractor 20 is expanded through the skin and tissue to an expanded configuration that increases the size of working channel 50 from proximal ends 26, 46 to distal ends 24, 44.

First portion 22 includes a semi-cylindrical body 23 extending between distal end 24 and proximal end 26. A collar 28 extends about proximal end 26, and forms a lip 28a extending about the outer surface of body 23. Second portion 42 includes a semi-cylindrical body 43 extending between distal end 44 and proximal end 46. A collar 48 extends about proximal end 46 of second portion 42, and defines a lip 48a extending about the outer surface of body 43. A first coupling member 30a pivotally couples a first side of first portion 22 to second portion 42 at their proximal ends 26, 46. A second coupling member 30b opposite first coupling member 30a pivotally couples the other side of first portion 22 to second portion 42 at their proximal ends 26, 46 along another side of retractor 20.

In the illustrated embodiment, first and second coupling members 30a, 30b are pins that extend through aligned holes or passageways provided through collars 28, 48 to pivotally couple first portion 22 to second portion 42. Other coupling arrangements are also contemplated at proximal ends 26, 46 of first and second portions 22, 42. For example, proximal end 26 of first portion 22 may be hingedly attached to proximal end 46 of second portion 42 with one or more hinges at each side of retractor 20. In another embodiment, at least the proximal ends of first portion 22 and second portion 42 are formed of a single piece of material and a resilient hinge couples first portion 22 to second portion 42 at their proximal ends 26, 46. Other embodiments contemplate a slotted arrangement extending around the proximal end of one of the retractor portions and one or more pins from the other retractor portion received in the slotted arrangement.

Figure 6:
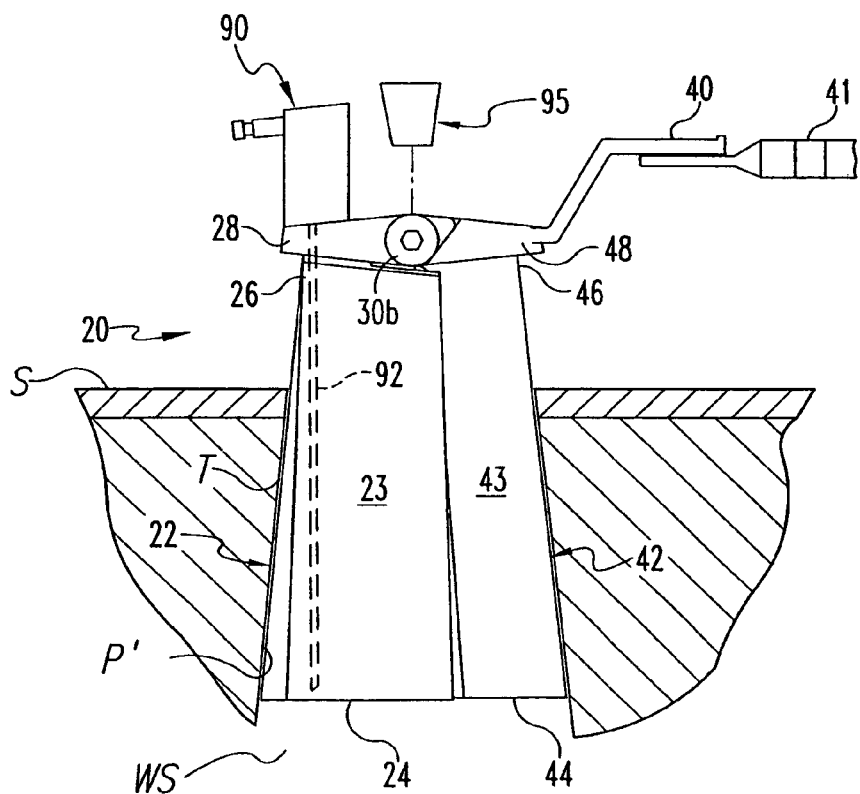
FIG. 6 is the retractor of FIG. 5 in an expanded configuration and with viewing instruments diagrammatically shown.

A bracket 40 extends from and is integrally formed with or attached to collar 48 of second portion 42. Bracket 40 can also be provided on collar 28 in lieu of or in addition to bracket 40 on collar 48. Bracket 40 extends away from working channel 50 and is connectable to one end of a flexible or articulatable arm 41 (FIG. 6.) The opposite end of arm 41 (not shown) can be mounted on the surgical table or other support device. Arm 41 supports retractor 20 in the patient yet allows percutaneous manipulation and re-positioning of retractor 20.

Body 23 of first portion 22 extends around at least a portion of body 43 of second portion 42. Body 23 has a perimeter length along distal end 24 which is greater than the perimeter length of body 23 at proximal end 26. Body 43 of second portion 42 includes a perimeter length along distal end 44 which is the same or can be about the same as the perimeter length of body 43 adjacent proximal end 46. Body 23 of first portion 22 can be flexible enough to extend around second portion 42 in form fitting relationship when retractor 20 is the unexpanded configuration of FIGS. 1 and 2 to minimize the profile of retractor 20. Body 23 flexes outwardly and rides along the outer surface of body 43 of second portion 42 as first portion 22 and second portion 42 are pivoted relative to one another to the expanded configuration of retractor 20.

In one specific embodiment, first portion 22 and second portion 42 are each made from surgical grade stainless steel. Other materials are also contemplated for bodies 23, 43, including, for example, plastics and metals and metal alloys, such as, for example, spring steel, shape memory metals and alloys, and aluminum. It is contemplated that body 23 can be provided with a cross-sectional thickness t1 that provides the desired flexibility, yet is sufficiently rigid to maintain retraction of the skin and tissue. Body 43 of second portion 42 can be provided with a thickness t2 that can be the same or greater than thickness t1 of first portion 22. The reduced thickness of body 23 provides it greater flexibility to flex inwardly and outwardly expand around body 43 of second portion 42. Thickness t2 provides second portion 43 greater rigidity to resist bending or bowing under the forces exerted on it by body 23 during and after movement of retractor 20 to its expanded configuration.

In the unexpanded configuration, working channel 50 has a generally circular cross-section along retractor 20, as best shown in FIG. 2. Working channel 50 has a first width D1 between the opposite edges of second portion 42 positioned in first portion 22. A second width D2 is defined between the mid-portions of first body 23 and second body 43 in the direction of expansion of first portion 22 relative to second portion 42. In the illustrated embodiment, first and second widths D1 and D2 are substantially the same since unexpanded working channel 50 has a generally circular cross-section. In the expanded configuration, as shown in FIG. 4, the portion of the expanded working channel 50 extending along the opposite edges of second body 43 maintains first width D1. However, first body 23 is flexed outwardly relative to second body 43, and defines a third width D3 between the sides of first body 23 that is greater than first width D1. In the expanded configuration of working channel 50, first body 23 and second body 43 define a fourth width D4 in the direction of expansion of first portion 22 relative to second portion 42 that is greater than second width D2. It is further contemplated that width D4 can be greater than widths D1 and D3.

Various configurations for working channel 50 are contemplated. In the unexpanded configuration, working channel 50 can have a cylindrical shape with, for example, a circular, oval, elliptical, or polygonal cross-section. In the expanded configuration, working channel 50 can have a frusto-conical shape with, for example a cross-section that is figure-eight or snowman shaped, oval, elliptical, circular or polygonal. In at least the direction of expansion, the size of the cross-section of working channel 50 decreases from distal end to the proximal end of retractor 20.

In one specific application for spinal surgery, it is contemplated that, after insertion of retractor 20, first portion 22 and second portion 42 are expanded predominantly in one direction to retract muscle and tissue along pathway P. For example, retractor 20 can be primarily or predominantly expandable in the direction of the spinal column axis. Since the muscle tissue adjacent the spine has a fiber orientation that extends generally in the direction of the spinal column axis, the expansion of retractor 20 separates the muscle tissue along the fibers, thus minimizing their separation and the resultant tearing and trauma to the muscle tissue is minimized. It is also contemplated in other techniques employing retractor 20 that working channel 50 expands primarily in a direction other than along the spinal column axis or in areas other than spine. Embodiments of retractor 20 are also contemplated in which working channel 50 is circular or polygonal in cross-section and expands substantially the same amount in all directions.

Figure 5:
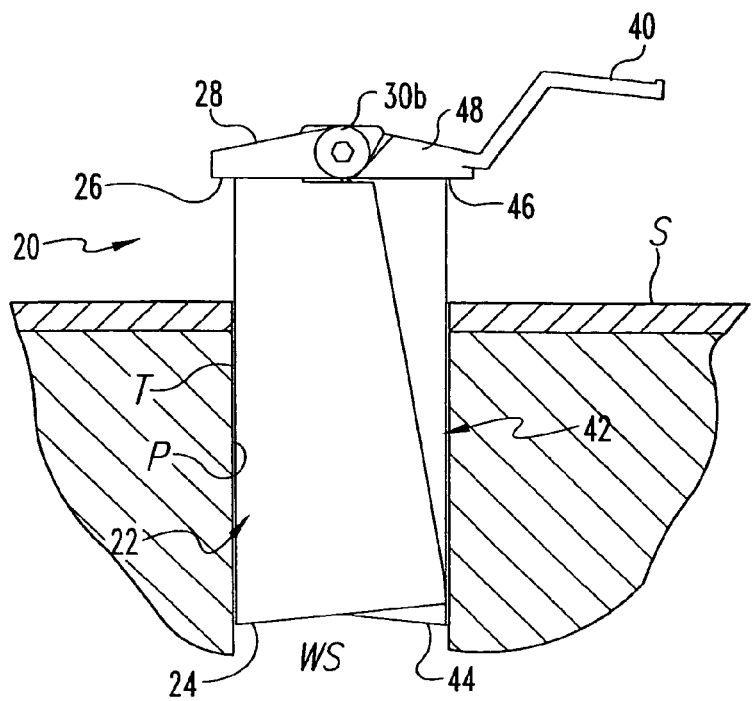
FIG. 5 is a side view of the retractor shown in FIG. 1 inserted through an incision in a patient with the retractor in an unexpanded configuration.

Referring now to FIGS. 5-6, positioning of retractor 20 through the skin S and tissue T of the patient will be described. An incision is made in skin S adjacent the location of a patient's anatomy to be accessed. For example, in spinal surgery, the incision can be made at a vertebral level at a location that provides access to the disc space between adjacent vertebrae or to one or more vertebra through a desired approach. Prior to insertion of retractor 20, skin S and tissue T can be sequentially dilated via guidewires and/or one or more dilators of increasing size to form a pathway P through skin S and tissue T to the surgical site in the patient. In such procedures, retractor 20 is positioned over the last inserted dilator in pathway P for retractor 20. Working channel 50 through retractor 20 provides access to a working space WS at the distal end of retractor 20 when the guidewires and dilators, if used, are removed therefrom.

For the entire surgery or for certain procedures, it may be desired by the surgeon to increase the size of working channel 50 to facilitate access working space WS below the distal end of retractor 20, or to even provide a greater working space WS. Retractor 20 can be pivoted from its unexpanded, insertion configuration to an expanded configuration as shown in FIG. 6. In the expanded configuration, first portion 22 and second portion 42 are pivoted away from one another about first and second coupling members 30a, 30b at proximal ends 26, 46. In the expanded configuration, pathway P' through skin S and tissue T is formed by first portion 22 and second portion 42. The size of working space WS can be increased while minimizing trauma to the tissue and skin along pathway P.

Working channel 50 has a tapered configuration that reduces in size from the distal end of retractor 20 adjacent working space WS through skin S to the proximal end of retractor 20. The tapered working channel provides the surgeon greater access and increased visualization of working space WS. The tapered working channel 50 also allows greater angulation of instruments placed through working channel 50, more selection in positioning of instruments within working channel 50, and the ability to position instruments adjacent the inner wall surfaces of the expanded first and second portions 22, 42, increasing the room available at working space WS for multiple instruments.

Viewing instruments can be positioned in or adjacent to working channel 50 to facilitate surgeon viewing of working space WS and the operative site. For example, an endoscopic viewing element 90 can be mounted on the proximal end of retractor 20 such that its scope portion 92 extends along working channel 50. A microscopic viewing element 95 can also be positioned over the proximal end of retractor 20 for viewing working space WS and the surgical site. Other imaging techniques, such as lateral fluoroscopy, can be used alone or in combination with the endoscopic and microscopic viewing elements. Further examples of such viewing instruments and mounting or orienting the same relative to retractor 20 are provided in U.S. patent application Ser. No. 09/815,963 filed on Mar. 23, 2001, which is hereby incorporated herein by reference in its entirety. It is further contemplated that other instruments can be mounted on the proximal end of retractor 20, such as nerve root retractors, tissue retractors, irrigation and/or aspiration instruments, illumination instruments and the like for use in surgical procedures through retractor 20 in the working space.

Figure 7:
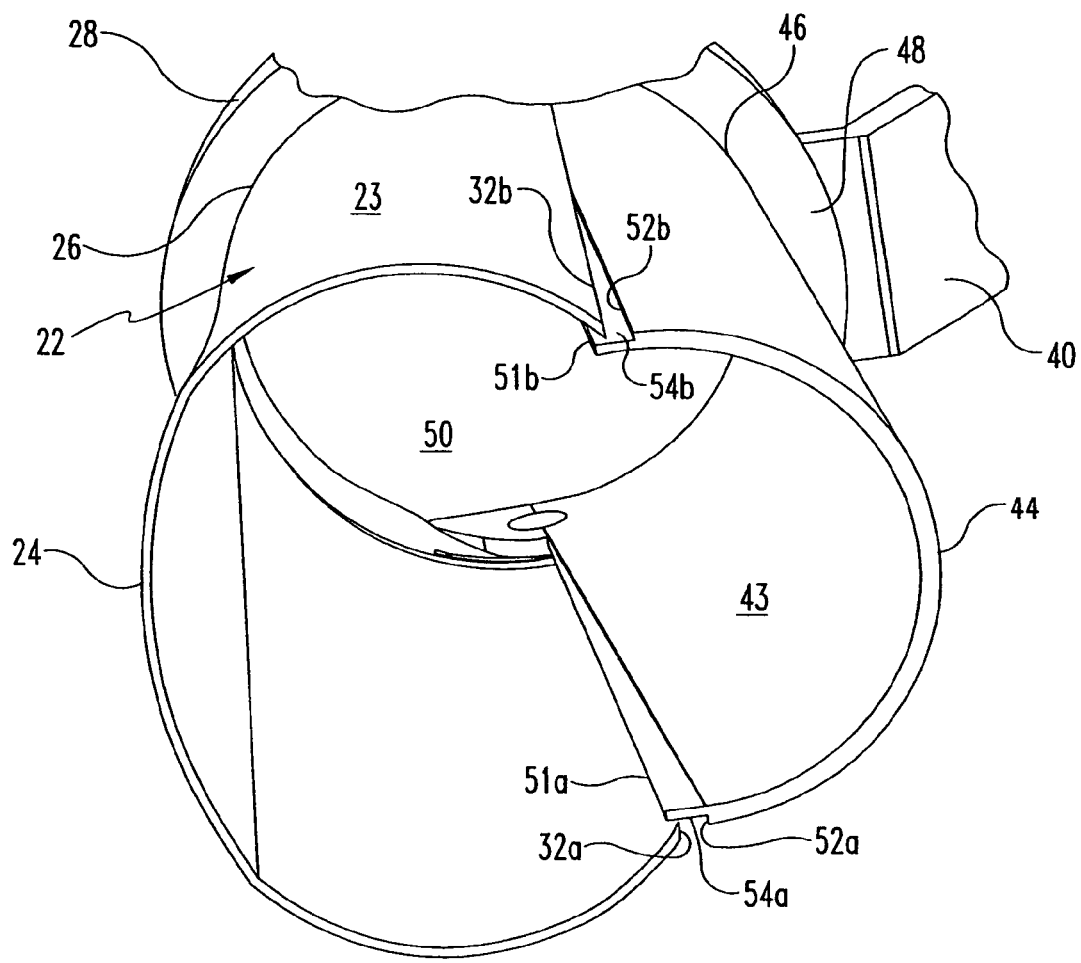
FIG. 7 is a perspective view looking toward the bottom of the expanded retractor of FIG. 3.

Referring now to FIG. 7, further details regarding the engagement of first portion 22 and second portion 42 when retractor 20 is in the expanded configuration will be provided. First body 23 of first portion 22 includes a first edge 32a extending between distal end 24 and proximal end 26. First body 23 of first portion 22 includes an opposite second edge 32b extending between distal end 24 and proximal end 26. Second portion 42 includes a first edge 51a extending along one side of second body 43 and an opposite second edge 51b extending along the opposite side of second body 43. First edge 51a includes a grooved portion 54a extending from distal end 44 along at least a portion of the length of first edge 51a. An engagement surface 52a extends along grooved portion 54a. Similarly, second edge 51b includes grooved portion 54b extending from distal end 44 along at least a portion of the length of second edge 51b. An engagement surface 52b extends along grooved portion 54b.

With retractor 20 in its expanded configuration, first edge 51a of second body 43 is is adjacent first edge 32a of first body 23, and second edge 51b of body 43 is adjacent second edge 32b of first body 23. First edge 32a resides at least partially in grooved portion 54a, and second edge 32b resides at least partially in grooved portion 52b. First edge 32a contacts engagement surface 52a along grooved portion 54a to maintain retractor 20 in its expanded configuration. Similarly, second edge 32b contacts engagement surface 52b in grooved portion 54b to maintain retractor 20 in its expanded configuration. The flexible second portion 22 tends to return toward its unexpanded configuration, thus first and second edges 32a, 32b frictionally engage the engagement surfaces extending along each of the grooved portions 54a, 54b. This locks first portion 22 with respect to second portion 42 in the expanded configuration, resisting collapse of the working channel by pressure of the surrounding tissue on first and second portions 22, 42 and facilitating manipulation of retractor 20 in the tissue without collapse of the working channel.

Other means for locking first and second portion 22, 42 in the expanded configuration are also contemplated. For example, second portion 42 can be provided with a ridge or protrusion at each of its opposite edges, and first portion 44 can engage the ridge or protrusion.

By maintaining a closed configuration for the working channel between first portion 22 and second portion 42 in the expanded configuration, migration of tissue into working channel 50 is prevented by the walls of first and second portions 22, 42. Other embodiments contemplate that working channel 50 is not completely enclosed.

Figure 8:
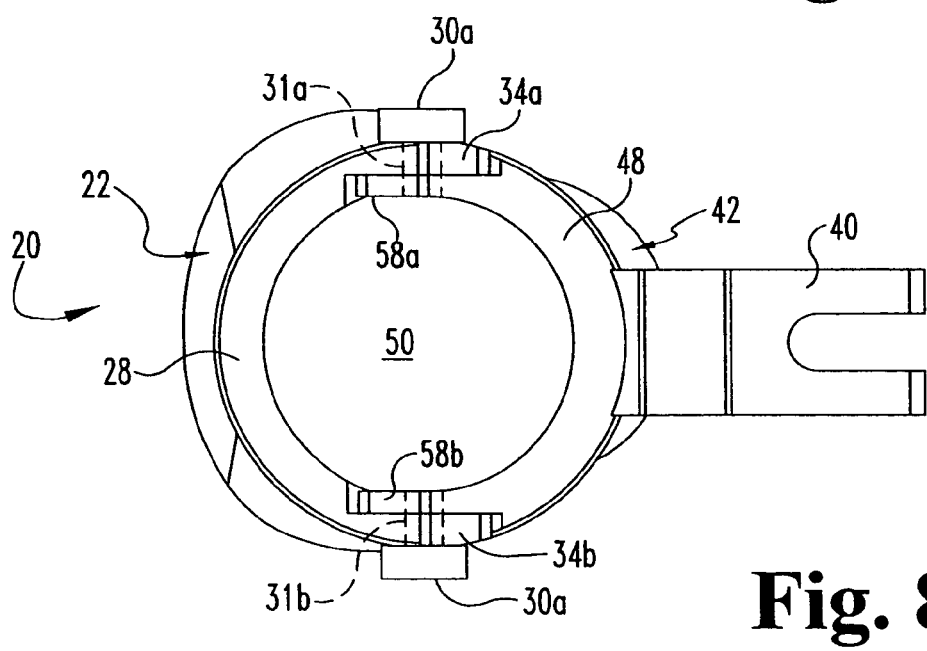
FIG. 8 is a top plan view of the expanded retractor of FIG. 3.
Figure 9:
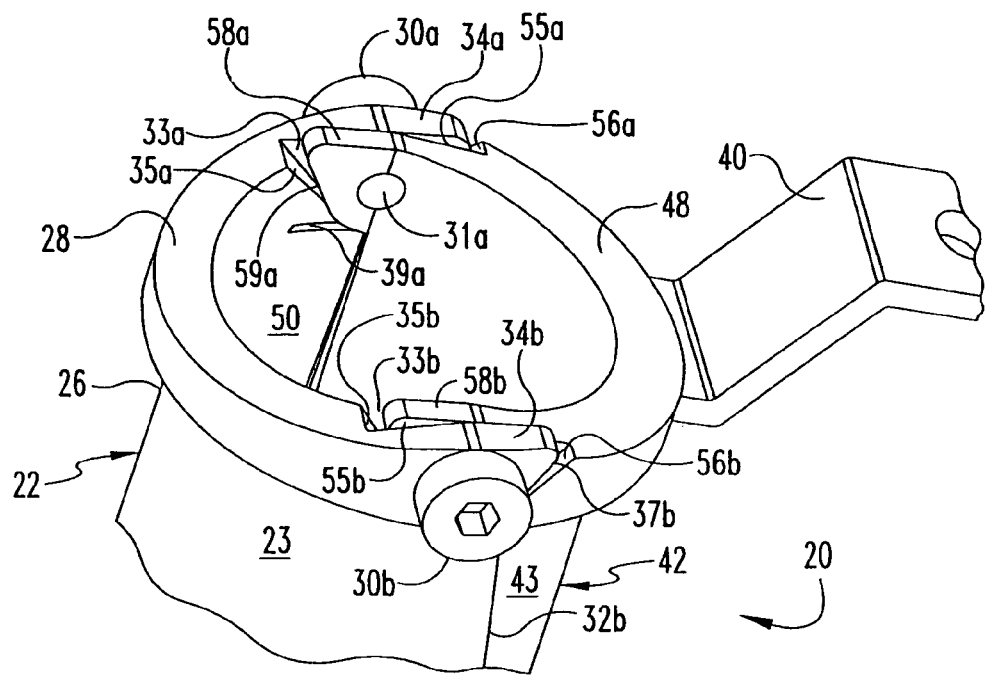
FIG. 9 is a perspective view of the upper portion of the unexpanded retractor of FIG. 1.
Figure 10:
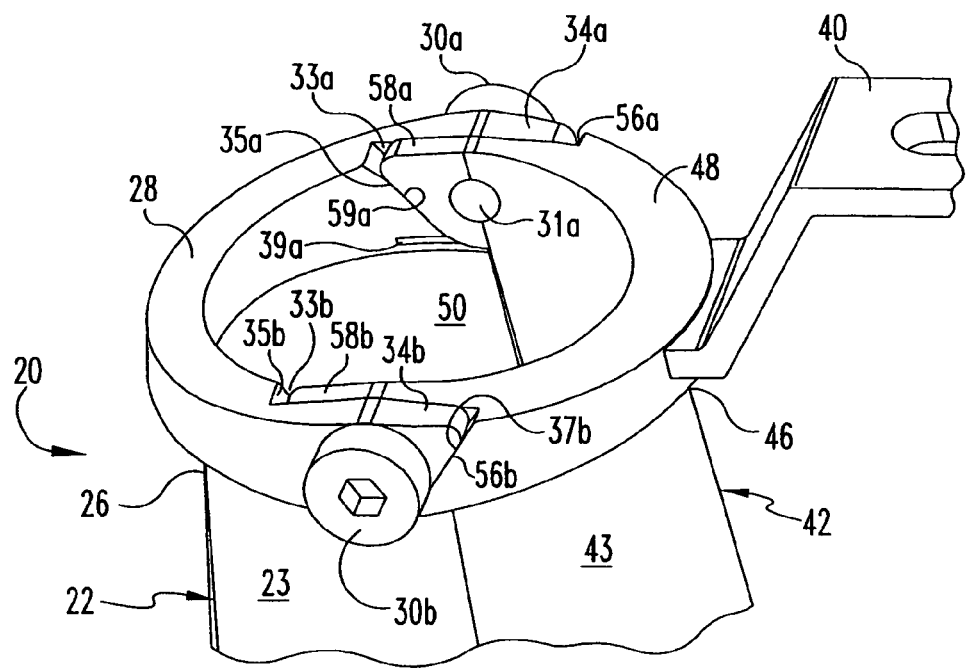
FIG. 10 is a perspective view of the upper portion of the expanded retractor of FIG. 3.

Referring now to FIGS. 8-10, further details regarding proximal ends 26, 46 of first and second portions 22, 42 will be described. Collar 28 includes a recess 33a formed adjacent first edge 32a on one side of first portion 22, and a second recess 33b opposite first recess 33a on the other side of first portion 22. Recess 33a includes an engagement surface 35a along an inner side thereof, and second recess 33b includes an engagement surface 35b extending along an inner side thereof. A first extension 34a extends along the outside of first recess 33a, and a second recess 34b extends along the outside of second recess 33b. First extension 34a and second extension 34b extend beyond the adjacent first edge 32a and second edge 32b, respectively, of body 23 of first portion 22.

Second portion 42 includes a first recess 55a along one side of second portion 42, and a second recess 55b along another side of second portion 42. First recess 55a includes an engagement surface 56a, and second recess 55b includes an engagement surface 56b. A first extension 58a extends along the inner side of first recess 55a, and a second extension 58b extends along the inner side of second recess 55b. First extension 58a includes an engagement surface 59a, and second extension 55b also includes a similarly situated engagement surface. First extension 58a resides within first recess 33a adjacent first extension 34a of first portion 22, and second extension 58b resides within second recess 33b adjacent second extension 34b of first portion 22. First coupling member 30a includes a pin extending through passage 31a of first extension 34a of first portion 22 and pivotally couples first extension 58a of second portion 42 thereto. Second coupling member 30b includes a pin extending through passage 31b of second extension 34b of first portion 22 and pivotally couples second extension 58b of second portion 42 thereto.

With retractor 20 in its unexpanded configuration as shown in FIG. 9, a gap is formed between engagement surfaces 35a, 35b of first portion 22 and engagement surfaces 59a, 59a of extensions 58a, 58b of second portion 42. As retractor 20 is moved to its expanded configuration as shown in FIG. 10, engagement surfaces 59a, 59a contact engagement surfaces 35a, 35b of first portion 22. Also, engagement surfaces 37a, 37b of extensions 34a, 34b of first portion 22 contact engagement surfaces 56a, 56b of second portion 42. The contact between the engagement surfaces of the recesses and extensions limit the pivotal movement of first portion 22 relative to second portion 42. First portion 22 can include a relieved portion 39a below first engagement surface 59a and a similar relief under second engagement surface 35b. The reliefs allow some flexing of engagement surfaces 35a, 35b to ensure engagement surfaces 59a, 59b of extensions 58a, 58b fully seat on engagement surfaces 35a, 35b.

Figure 11:
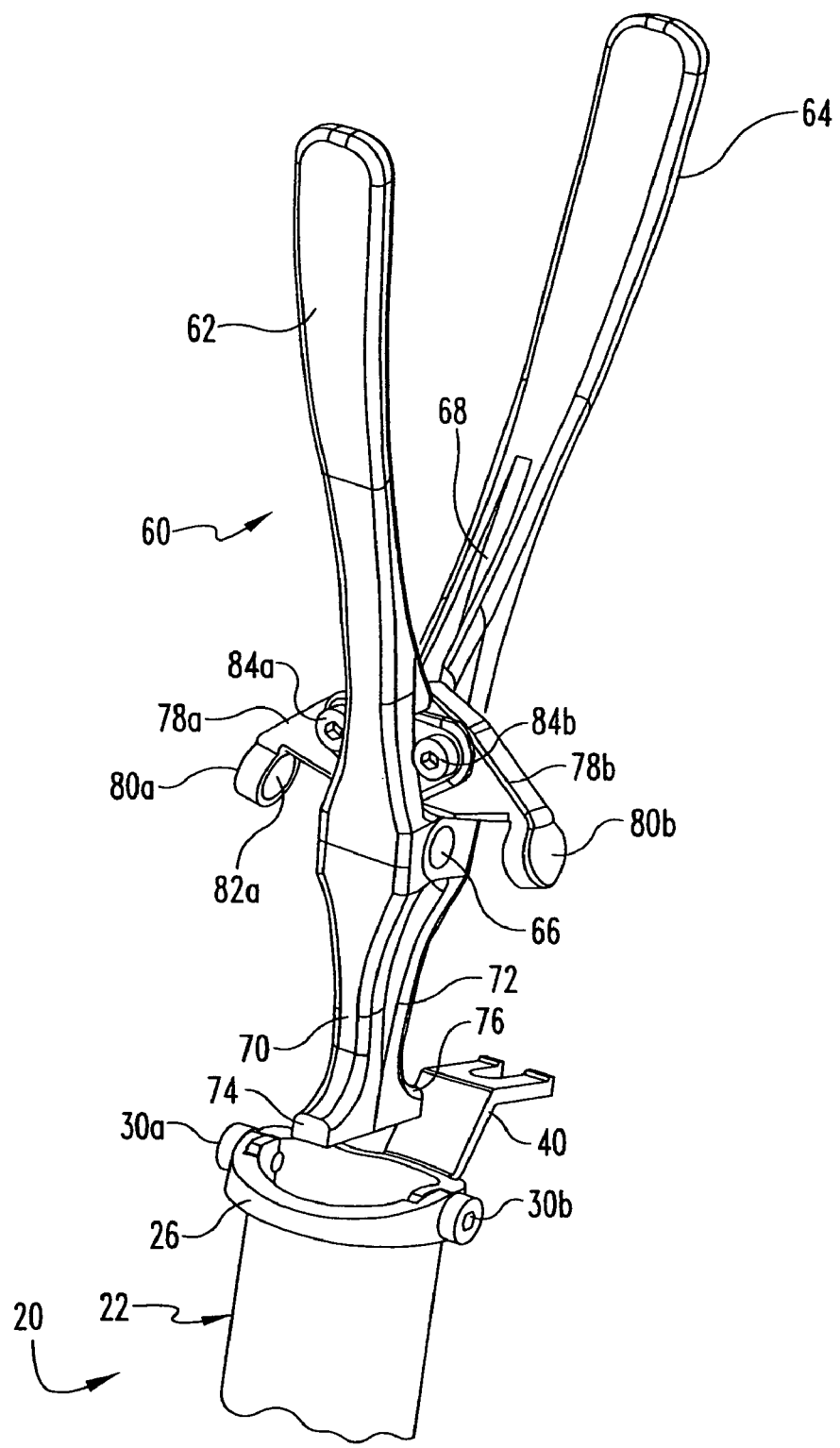
FIG. 11 is a perspective view of the upper portion of the unexpanded retractor of FIG. 1 with an expansion instrument positioned adjacent thereto.
Figure 12:
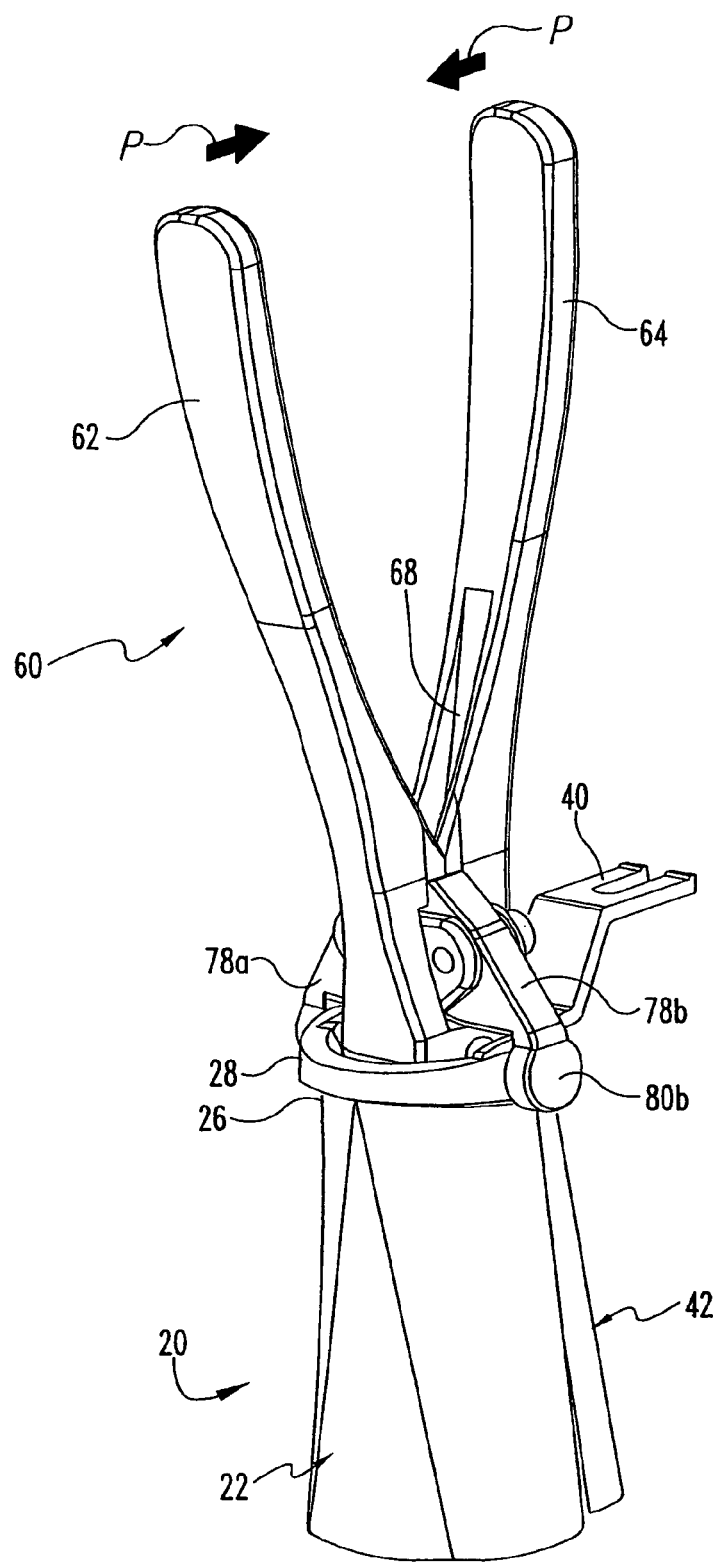
FIG. 12 is a perspective view of the retractor of FIG. 3 with the expansion instrument of FIG. 11 positioned therein to move the retractor to its expanded configuration.

Referring now to FIGS. 11-12 there is shown retractor 20 with an expansion instrument 60. Expansion instrument 60 includes a first handle 62 pivotally coupled to a second handle 64 with pin 66. A leaf spring 68 can extend between first handle 62 and second handle 64 to bias handles 62, 64 in a closed position as shown in FIG. 11. Extending distally from the pivotal connection of first handle 62 and second handle 64 are first distal portion 70 and second distal portion 72, respectively. Distal portion 70 includes a foot 74 at a distal end thereof, and distal portion 72 includes a foot 76 at a distal end thereof. Feet 74, 76 extend toward first portion 22 and second portion 42, respectively when expansion instrument 60 is inserted in working channel 50 of retractor 20.

Expansion instrument 60 includes a first arm 78a and a second arm 78b above pin 66. First arm 78a is pivotally coupled to first and second handles 62, 64 via coupler 84a, and second arm 78b is pivotally coupled to first and second handles 62, 64 via coupler 84b. First and second arms 78a, 78b extend transversely to the orientation of feet 74, 76. First arm 78a includes an engagement member 80a having a receptacle 82a positionable over the head of first coupling member 30a. Second arm 78b includes an engagement member 80b having a receptacle positionable over the head of second coupling member 30b.

As shown in FIG. 12, expansion instrument 60 is mountable on retractor 20 by pivoting first arm 78a so that first coupling member 30a is captured in receptacle 82a of engagement member 80a, and second coupling member 30b is captured in receptacle 82b of engagement member 80b. The engagement of expansion instrument 60 to retractor 20 ensures that expansion instrument 60 is not inserted too far into working channel 50 before and during insertion, and allows the application a steady and uniform expansion force without expansion instrument 60 slipping relative to retractor 20. With expansion instrument 60 mounted on retractor 20, handles 62, 64 are pressed toward one another in order to move feet 74, 76 away from one another transverse to the pivot axis of first portion 22, second portion 42 and into contact with adjacent first portion 22 and second portion 42. Feet 74, 76 apply a force on first portion 22 and second portion 42 to pivot first and second portions 22, 42 about their proximal ends to move retractor 20 to its expanded configuration. Retractor 20 can be locked in the expanded configuration by engagement of edges 32a, 32b of first portion 22 with the respective engagement surfaces of second portion 42.

To collapse retractor 20 to its unexpanded configuration, expansion instrument 60 is rotated 90 degrees so the feet 74,76 can apply an expansion force to first portion 22 in the direction of the pivot axis of first portion 22 and second portion 42. The expansion of first portion 22 in this direction disengages or unlocks edges 32a, 32b from engagement surfaces 52a, 52b of second portion 42 and allows first portion 22 and second portion 42 to pivot relative to one another to unexpand retractor 20. Retractor 20 can then be withdrawn from the tissue in its unexpanded condition, minimizing pressure on the adjacent tissue as retractor 20 is withdrawn.

Referring now to FIGS. 13a-13d, there is shown another embodiment expansion instrument 60'. Except as otherwise provided, expansion instrument 60' can be similar to expansion instrument 60 discussed above, and like elements between expansion instruments 60 and 60' are designated with the same reference numeral. Expansion instrument 60' includes a movable foot 74' coupled to distal portion 70'. In the illustrated embodiment, foot 74' is rotatable about pin 75' relative to distal portion 70' in order to position selected ones of the retractor portion contact surfaces 74a', 74b' or 74c' adjacent one of the retractor portions 22, 42.

Figure 13A:
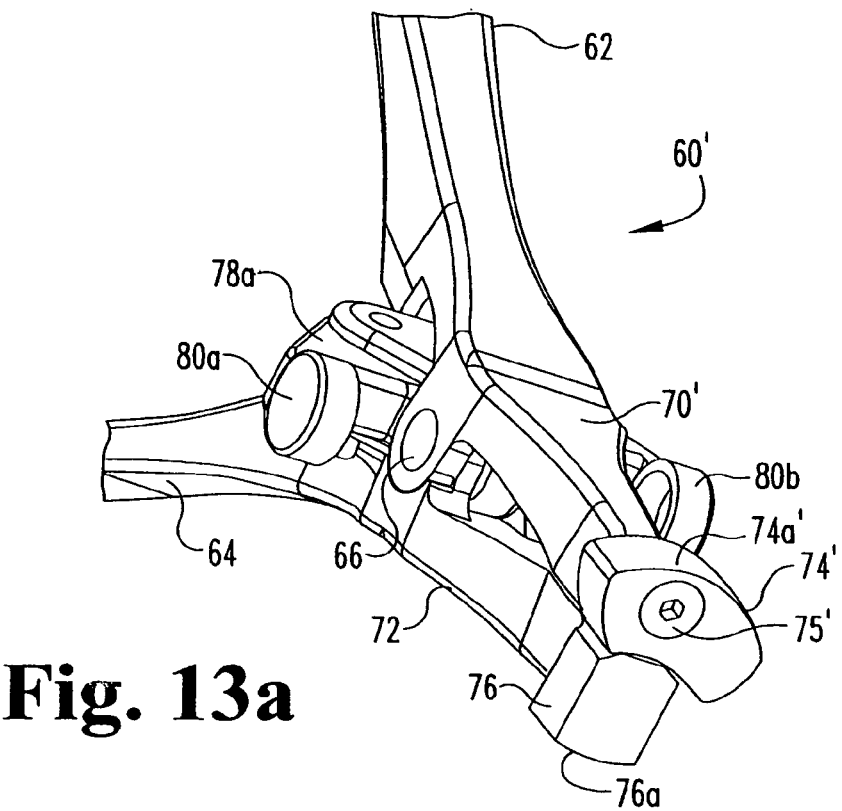
FIGS. 13a-13d illustrate another embodiment expansion instrument having an adjustable foot.
Figure 13B:
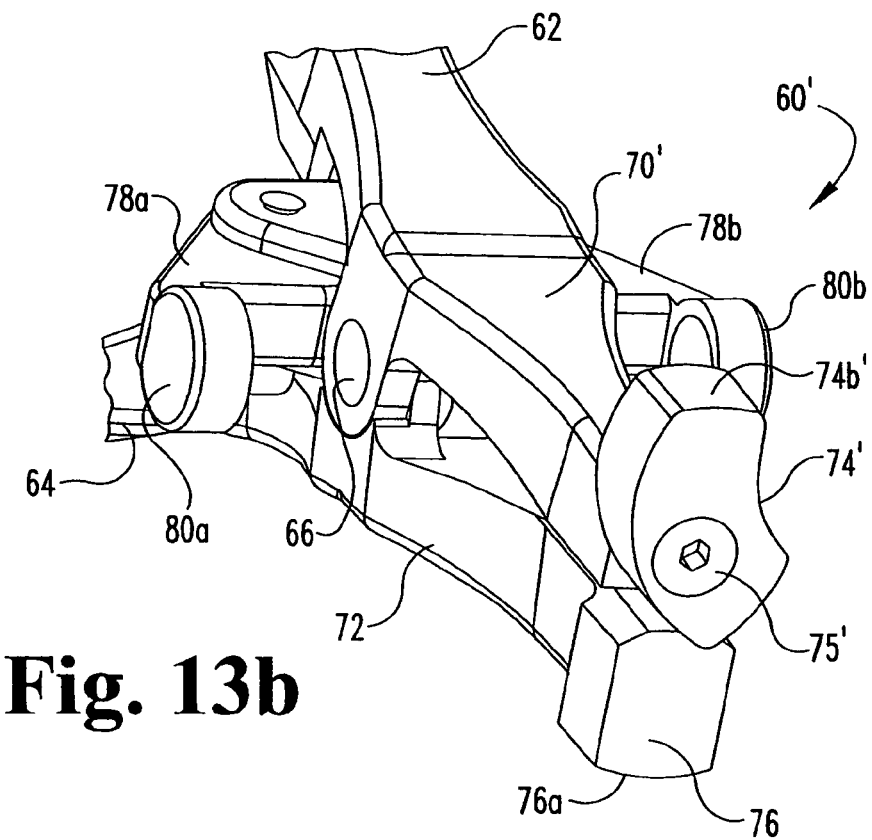
Figure 13C:
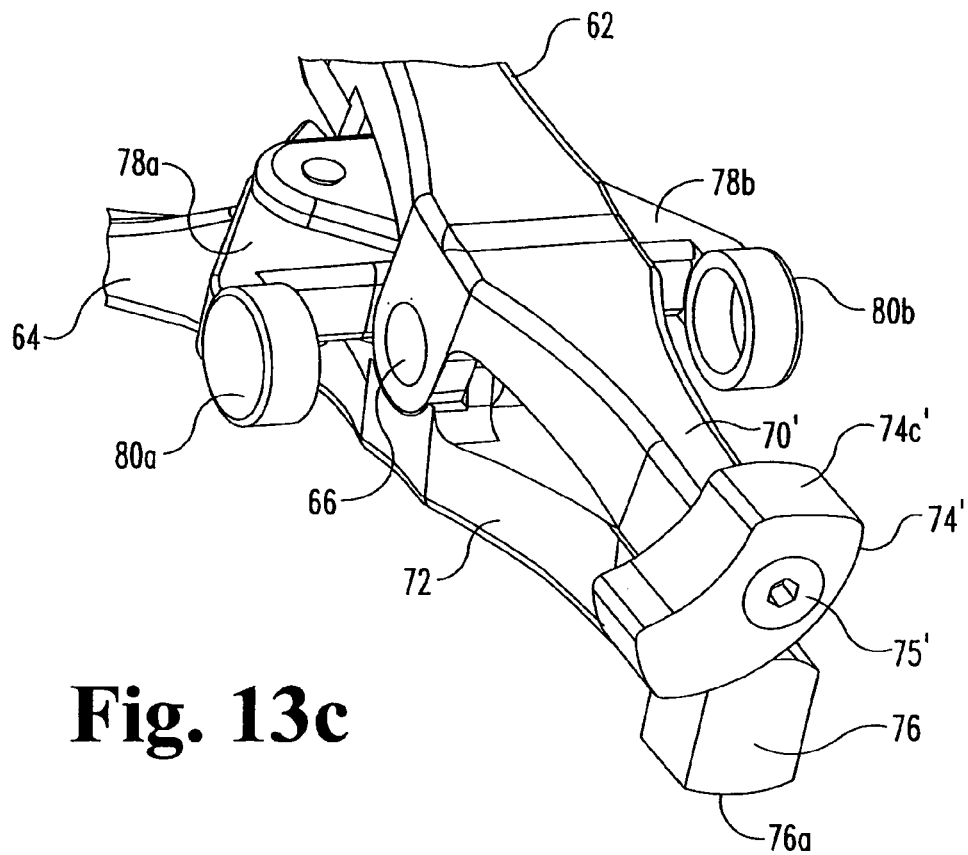
Figure 13D:
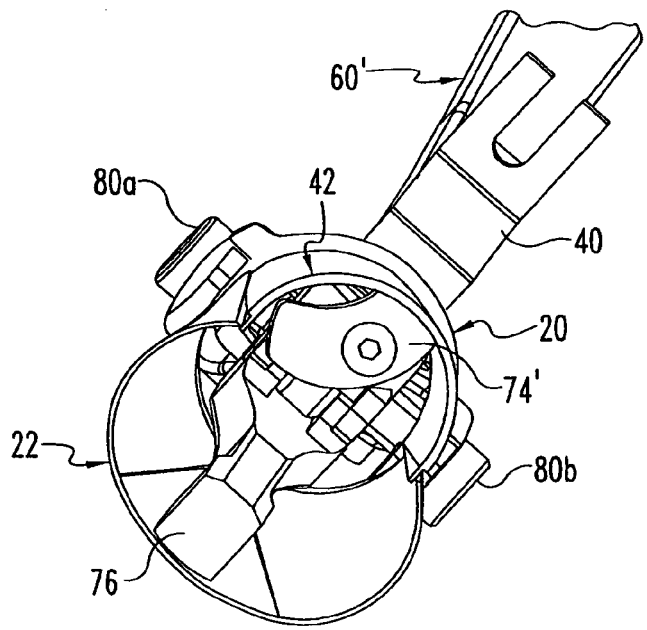

The contact surfaces 74a', 74b' and 74c' are located at differing distances from pin 75' to allow the surgeon to select the desired amount of expansion for retractor 20. Foot 74' is rotated about pin 75' to select the desired contact surface by orienting the desired contact surface away from contact surface 76a of foot 76. For example, as shown in FIG. 13a, contact surface 74a' is selected to provide minimum expansion since it is located closest to pin 75'. In FIG. 13b contact surface 74b' is selected to provide maximum expansion since it is located furthest away from pin 75'. In FIG. 13c contact surface 74c' is selected to provide intermediate expansion since it has a distance from pin 75' that is between the distances of contact surface 74a' and contact surface 74b'. FIG. 13d shows expansion instrument 60' mounted on retractor 20 with contact surface 74c' of foot 74 in contact with second portion 42 and contact surface 76a of foot 76 in contact with first portion 22 of retractor 20.

It is further contemplated that the amount of expansion provided by each of the contact surfaces 74a', 74b' and 74c' can correspond to a particular retractor length. For example, with expansion instrument 60' mounted on the retractor, the depth which expansion instrument 60' extends into the retractor is the same no matter the length of the retractor. Thus, to provide the same size opening at the distal end of the retractor, the first and second portions of a shorter retractor will be separated a greater amount at the depth of feet 74', 76 than will a longer retractor. Accordingly, contact surface 74a' can be selected for a longer length retractor, contact surface 74b' can be selected for a shorter length retractor, and contact surface 74c' can be selected for an intermediate length retractor.

Of course, expansion instruments 60, 60' can be oriented so that feet 74, 74' contact first portion 22 and foot 76 contacts second portion 42. It is further contemplated that expansion instruments 60, 60' can be provided so that they are not mountable on the retractor, but rather are held in position at the desired depth in the retractor for expansion of the retractor.

It is contemplated that for spinal surgery various retractors 20 can be provided in a kit with lengths ranging from 20 millimeters to 100 millimeters in increments of 10 or 20 millimeters. It is further contemplated that retractor 20 can be provided in a kit with various diameters, such as 14, 16, 18, 20, 21 or 25 millimeters in its unexpanded configuration. It should be understood, however, that the present invention contemplates that retractor 20 can have other lengths and diameters and can be provided in a kit with different increments. The appropriate length for retractor 20 will depend on the depth of the desired surgical location below the skin S of the patient, the anatomical location of the surgery, and the patient's anatomy. These factors in retractor selection can be evaluated through pre-operative planning prior to surgery by x-rays or other known imaging technique, and can be adjusted during the surgical procedure if necessary since retractors of differing lengths and diameters can be made available.

Figure 14A:
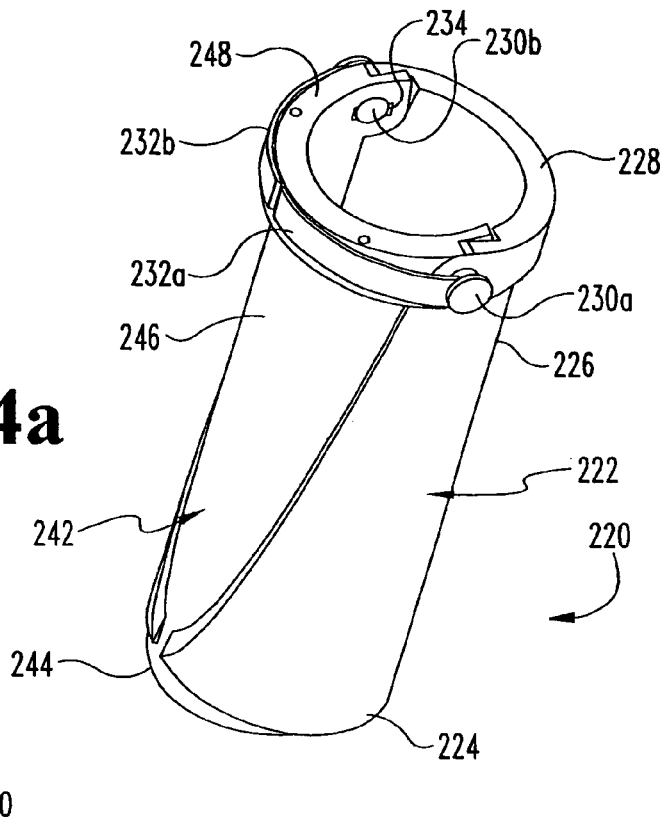
FIGS. 14a-14c illustrate another embodiment expandable retractor and a coupling member comprising a portion thereof.
Figure 14C:
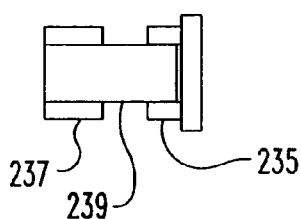
Figure 14B:
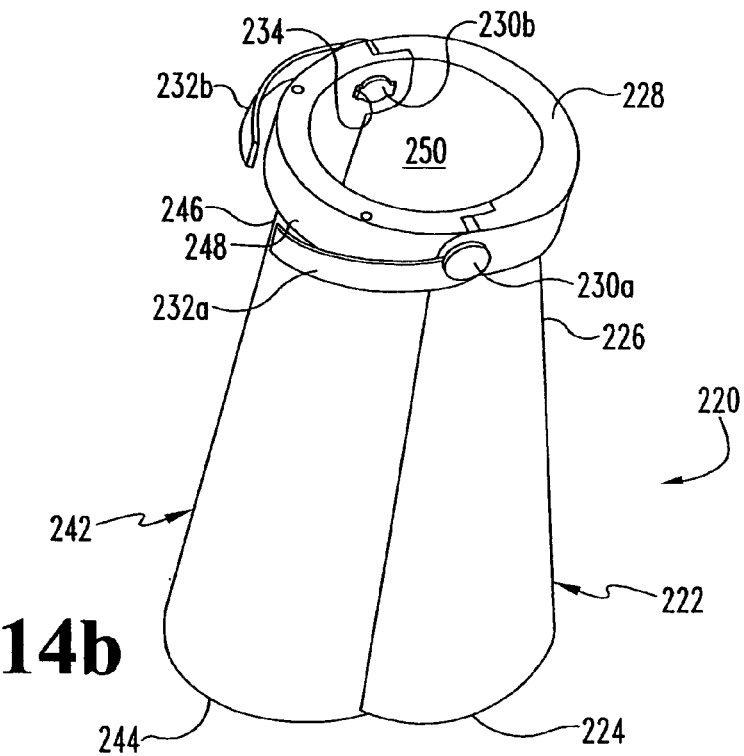

In FIGS. 14*a*-14*b*, there is shown another embodiment expandable retractor 220. In FIG. 14*a*, retractor 220 is in its unexpanded configuration and in FIG. 14*b* retractor 220 is in its expanded configuration. Retractor 220 is similar in many respects to retractor 20 discussed above. Retractor 220 includes a first portion 222 having a distal end 224, a proximal end 226, and a collar 228 at proximal end 226. Retractor 220 further includes a second portion 242 having a distal end 244, a proximal end 246, and a collar 248 at proximal end 246. First coupling member 230*a* and second coupling member 230*b* pivotally couple first portion 222 to second portion 242. A first lever arm 232*a* is connected with and extends from first coupling member 230*a* around collar 248, and a second lever arm 232*b* is connected with and extends from second coupling member 230*b* around collar 248.

In the unexpanded configuration, lever arms 232*a*, 232*b* are adjacent collar 248, and coupling members 230*a*, 230*b* project outwardly from collar 228 as shown in FIG. 14*a*. Coupling members 230*a*, 230*b*, as shown in FIG. 13*c*, have a first keyed portion 237 configured to engage slotted hole 234 of collar 248. The cylindrical portions 239 of coupling members 230*a*, 230*b* rotatably reside in the slotted hole (not shown) extending through collar 228 of first portion 222. This allows first portion 222 to be pivoted relative to second portion 242 about coupling members 230*a*, 230*b*.

When first portion 222 is pivoted relative to second portion 242 to the expanded configuration, the slotted portions of slotted hole 234 and the slotted hole through collar 228 are aligned. Coupling members 230*a*, 230*b* can be pressed inwardly so that a second keyed portion 235 of coupling members 230*a*, 230*b* engages the slotted hole formed through collar 228, while the first keyed portion 237 remains engaged in slotted hole 234 of collar 248, thus fixing first portion 222 relative to second portion 242. Lever arms 232*a*, 232*b* extend away from collar 248 when first portion 222 is locked relative to second portion 242. To move retractor 220 to the unexpanded configuration, lever arms 232*a*, 232*b* are pressed toward collar 248 to move coupling members 230*a*, 230*b* and their second keyed portions 235 out of engagement with the slotted holes in collar 228 of first portion 222. First portion 222 can then pivot toward second portion 242 to collapse retractor 220 for withdrawal from the patient.

In this embodiment, rather than providing an engagement surface along the opposite edges of second portion 242, the keyed engagement of coupling members 230*a*, 230*b* and first and second portions 222, 242 locks retractor 220 in its expanded configuration. However, the provision of a grooved portion and engagement surface is not precluded.

Other means for maintaining first and second portions of the retractor in an expanded configuration are also contemplated. For example, in FIGS. 15*a*-15*c* another embodiment expandable retractor 120 is shown with a ratchet and pawl type mechanism at the proximal ends of first portion 122 and second portion 142. In this embodiment, rather than providing a grooved portion and engagement surface along the opposite edges of second portion 142, the ratchet and pawl mechanism maintains retractor 120 in its expanded configuration. However, the provision of a grooved portion and engagement surface is not precluded.

Figure 15A:
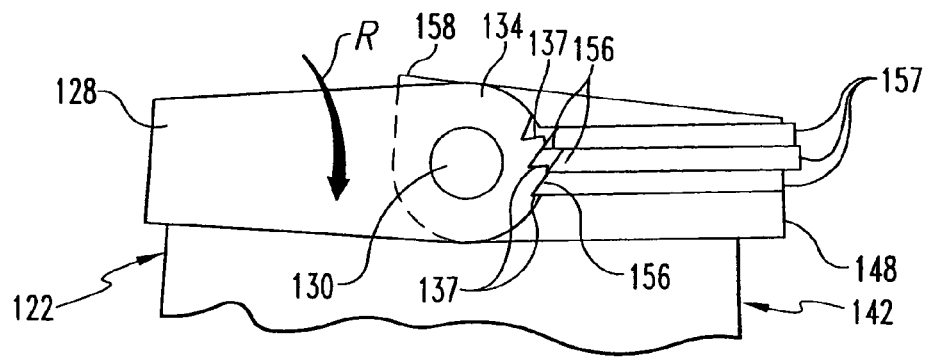
FIGS. 15a-15c illustrate the proximal end of yet another embodiment expandable retractor.
Figure 15B:
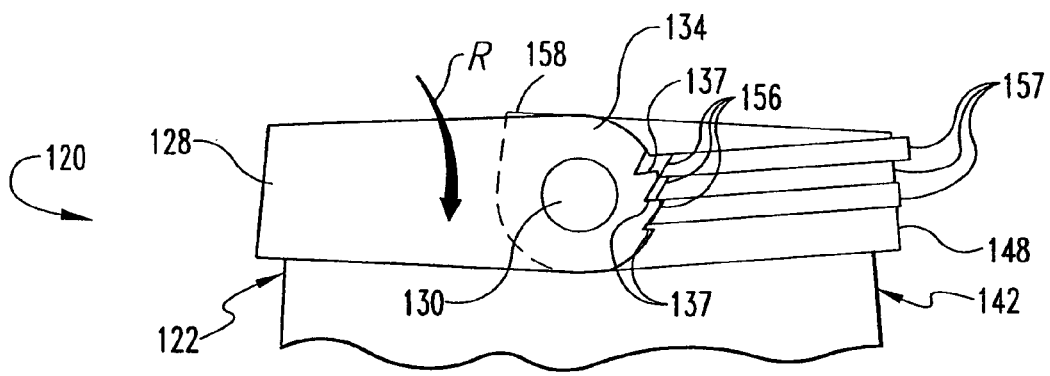
Figure 15C:
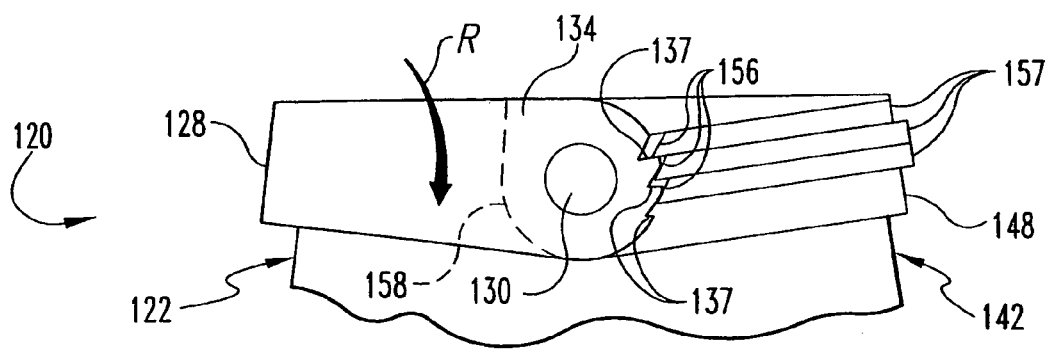

First portion 122 includes a collar 128 at its proximal end. Collar 128 includes an extension 134 extending from each side thereof, it being understood that only one side is shown in FIGS. 15*a*-15*c*. Similarly, second portion 142 includes an extension 158 extending from each side thereof that is positionable alongside extension 134 of first portion 122, it being understood that only one side is shown in FIGS. 15*a*-15*c*. A pin 130 pivotally couples extensions 134, 158 to one another. Extension 134 includes a number of teeth 137 formed at the end thereof that are engageable with ends 156 of pawls 157 extending around collar 148. Pawls 157 are biased into engagement with teeth 137 and moveable relative to collar 148 for disengagement of ends 156 with teeth 137.

When in the unexpanded configuration (not shown) teeth 156 are not engaged by any of the pawls 157. In FIG. 15*a*, retractor 120 is expanded by pivoting first portion 122 in the direction of arrow R relative to second portion 142 so that lower pawl 157 is biased into engagement with lower tooth 137. In FIG. 15*b*, first portion 122 is further pivoted in the direction of arrow R relative to second portion 142 to expand retractor 120 with the end 156 of middle pawl 157 in engagement with the middle tooth 137. In FIG. 15*c* first portion 122 is further pivoted in the direction of arrow R relative to second portion 142 to expand retractor 120 with the end 156 of upper pawl 157 in engagement with the upper tooth 137. It is contemplated that teeth 137 and pawls 157 can be spaced so that retractor 120 is expanded incrementally. In one specific embodiment, the teeth 136 and pawls 157 are spaced so that first portion 122 is pivoted in 5 degree increments relative to second portion 142, ranging from 0 degrees to 15 degrees. Other increments are also contemplated.

FIGS. 16*a*-16*b* illustrate another embodiment retractor 320 that is similar to retractor 20 but includes another proximal end configuration. In FIG. 16*b*, retractor 320 is in its unexpanded configuration and in FIG. 16*a* retractor 320 is in its expanded configuration. Retractor 320 includes a first portion 322 having a distal end 324, a proximal end 326, and a collar 328 at proximal end 326. Retractor 320 further includes a second portion 342 having a distal end 344, a proximal end 346, and a collar 348 at proximal end 346. First coupling member 330*a* and second coupling member 330*b* pivotally couple first portion 322 to second portion 342 about a pivot axis A. Collars 328, 348 have a height that is less than the height of collars 28, 48 of retractor 20, reducing the retractor length. Viewing instruments and other instruments can be positioned in, over, and/or attached to retractor 320 as discussed above with respect to retractor 20.

Collar 328 includes a first extension 334*a* extending along one side thereof and above collar 328, and a second extensions 334*b* extending along the other side thereof and above collar 328. First extension 334*a* and second extension 334*b* are offset laterally with respect to collar 328 to form recesses for receiving respective ones of the extensions 358*a*, 358*b* of collar 348 therealong so that extensions 358*a*, 358*b* do not protrude into the working channel of retractor 320. Extensions 358*a*, 358*b* extend above collar 348. Aligned holes are provided through adjacent extensions 334*a*, 358*a* and adjacent extensions 334*b*, 358*b* to receive coupling members 330*a*, 330*b*. Pivot axis A is thus offset proximally from the proximal ends of collars 328, 348 so that first portion 322 and second portion 342 are expandable through their respective proximal ends to coupling members 330a, 330b.

Collar 328 includes a first contact surface 335a below first extension 358a of collar 348, and a second contact surface 335b below second extension 358b of collar 348. Collar 348 includes a first lateral extension 356a that provides a contact surface below first extension 334a of collar 328, and an opposite second lateral extension that provides a contact surface below second extension 334b of collar 328. With retractor 320 in its unexpanded configuration as shown in FIG. 16b, a gap is formed between the adjacent extensions and engagement surfaces of collars 328, 348. When retractor 320 is expanded sufficiently, extensions 334a, 334b engage respective ones of the contact surfaces of collar 348, and extensions 358a, 358b engage respective ones of the contact surfaces of collar 328, preventing over-expansion of retractor 320.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, certain embodiments contemplate that the first and second portions of the retractor are not provided with proximal end collars. Other embodiments contemplate the first and second portions are not pivotally coupled to one another, but rather to intermediate members extending between the first and second portions along each side of the retractor.

What is claimed is:

1. A kit for use in percutaneous surgery, comprising:
   a retractor having a working channel extending between a proximal end and a distal end of said retractor, said retractor having a first portion coupled to a second portion, said first and second portions movable relative to one another for engagement in an expanded configuration, wherein:
      said first portion and said second portion each include opposite edges extending between a proximal end and a distal end thereof;
      said second portion includes an engagement surface extending along at least a portion of each of said opposite edges thereof;
      in said unexpanded configuration said edges of said first portion extend around said second portion;
      in said expanded configuration said opposite edges of said first portion engage adjacent ones of said engagement surfaces of said second portion;
   an expansion instrument positionable in said working channel and engageable with said first portion and said second portion to move said first and second portions to said expanded configuration, wherein with said working channel in said expanded configuration said expansion instrument is positionable in said working channel to disengage said first and second portions for movement to an unexpanded configuration and
   a series of tubular tissue dilators positionable one over the other to sequentially dilate bodily tissue, wherein said working channel of said retractor is sized for positioning about said tissue dilators when in an unexpanded configuration.

2. The kit of claim 1, wherein said first portion is pivotally coupled to said second portion at said proximal end of said retractor and said first and second portions are pivotal between said unexpanded configuration and said expanded configuration.

3. The kit of claim 1, wherein said expansion instrument is mountable on a proximal end of said retractor.

4. A kit for use in percutaneous surgery, comprising:
   a retractor having a working channel extending between a proximal end and a distal end of said retractor, said retractor having a first portion coupled to a second portion in an unexpanded configuration, wherein said first and second portions are movable relative to one another for engagement in an expanded configuration to expand said working channel between said proximal and distal ends, wherein said working channel has a generally circular cross-section in said unexpanded configuration and in said expanded configuration said first and second portions define said working channel with a first width between opposite edges of said first and second portions and said first and second portions define a second width in a direction of expansion of the first and second portions that is transverse to said first width and greater than said first width, wherein said first width and said second width are measured on the same plane, where the plane is orthogonal to the longitudinal axis of said retractor;
   a series of tubular tissue dilators positionable one over the other to sequentially dilate bodily tissue, wherein said working channel of said retractor is sized for positioning around said tissue dilators when said retractor is in said unexpanded configuration; and
   an expansion instrument positionable in said working channel and engageable with said first portion and said second portion to move said first and second portions to said expanded configuration.

5. The kit of claim 4, wherein said first portion substantially envelopes said second portion in said unexpanded configuration.

6. The kit of claim 4, wherein said first portion is pivotally coupled to said second portion at proximal ends of said first and second portions and in said expanded configuration distal ends of said first and second portions are pivoted away from one another about said pivotally coupled proximal ends.

7. The kit of claim 4, wherein said first portion is pivotally coupled to said second portion along a pivot axis located proximally of proximal ends of said first portion and said second portion.

8. The kit of claim 4, wherein when in said expanded configuration:
   said working channel tapers in size from said distal end to said proximal end; and
   said second portion includes opposite edges extending between distal and proximal ends of said second portion that overlap adjacent edges of said first portion adjacent a distal end of said first portion.

9. The kit of claim 4, wherein said retractor forms a tubular body in said unexpanded configuration and said series of tissue dilators includes a series of elongated tubes of increasing diameter.

10. The kit of claim 4, wherein in both said expanded and said unexpanded configurations said first portion and said second portion enclose said working channel between said proximal and distal ends of said working channel.

11. A kit for use in percutaneous surgery, comprising:
    a retractor having a working channel extending between a proximal end and a distal end of said retractor, said retractor having a first portion coupled to a second portion in an unexpanded configuration, wherein said first and second portions are movable relative to one another for engagement in an expanded configuration to expand said working channel between said proximal and distal ends, wherein:

said first portion and said second portion each include opposite edges extending between a proximal end and a distal end thereof;

said second portion includes an engagement surface extending along at least a portion of each of said opposite edges thereof;

in said unexpanded configuration said edges of said first portion extend around said second portion;

in said expanded configuration said opposite edges of said first portion engage adjacent ones of said engagement surfaces of said second portion; and a series of tubular tissue dilators positionable one over the other to sequentially dilate bodily tissue, wherein said working channel of said retractor is sized for positioning around said tissue dilators when said retractor is in said unexpanded configuration.

* * * * *